(12) United States Patent
Ishikura et al.

(10) Patent No.: US 9,168,241 B2
(45) Date of Patent: Oct. 27, 2015

(54) COMPOSITIONS AMELIORATING A REDUCED DIURNAL ACTIVITY AND/OR DEPRESSIVE SYMPTOMS

(75) Inventors: Yoshiyuki Ishikura, Ibaraki (JP); Yoshihiko Koga, Tokyo (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 484 days.

(21) Appl. No.: 11/922,937

(22) PCT Filed: Jun. 29, 2006

(86) PCT No.: PCT/JP2006/313444
§ 371 (c)(1),
(2), (4) Date: Dec. 27, 2007

(87) PCT Pub. No.: WO2007/004689
PCT Pub. Date: Jan. 11, 2007

(65) Prior Publication Data
US 2009/0226481 A1 Sep. 10, 2009

(30) Foreign Application Priority Data
Jun. 30, 2005 (JP) ................. 2005-191506

(51) Int. Cl.
*A61K 31/202* (2006.01)
*A61K 36/07* (2006.01)
*A61K 36/06* (2006.01)
*A61K 36/062* (2006.01)
*A23L 1/30* (2006.01)

(52) U.S. Cl.
CPC ............ *A61K 31/202* (2013.01); *A23L 1/3008* (2013.01); *A61K 36/06* (2013.01); *A61K 36/062* (2013.01); *A61K 36/07* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,526,902 A | 7/1985 | Rubin | |
| 4,668,704 A | 5/1987 | Hollander et al. | |
| 5,198,468 A | 3/1993 | Horrobin | |
| 5,583,019 A | 12/1996 | Barclay | |
| 5,866,703 A | 2/1999 | Horrobin et al. | |
| 5,902,807 A | 5/1999 | Haapalinna et al. | |
| 6,034,130 A | 3/2000 | Wang et al. | |
| 6,069,138 A | 5/2000 | Ponroy | |
| 6,080,787 A | 6/2000 | Carlson et al. | |
| 6,225,444 B1 | 5/2001 | Shashoua | |
| 2002/0040058 A1 | 4/2002 | Kiliaan et al. | |
| 2003/0040542 A1 | 2/2003 | Martin | |
| 2004/0219208 A1 | 11/2004 | Kawamura et al. | |
| 2004/0266874 A1 | 12/2004 | Akimoto et al. | |
| 2006/0057185 A1 | 3/2006 | Akimoto et al. | |
| 2006/0088573 A1 | 4/2006 | Ishikura et al. | |
| 2006/0217368 A1 | 9/2006 | Morishita et al. | |

FOREIGN PATENT DOCUMENTS

| | | |
|---|---|---|
| CA | 2109777 | 5/1994 |
| CA | 2596241 | 12/1994 |
| CA | 2 512 133 | 5/2005 |
| CN | 1155982 A | 8/1997 |
| CN | 1175976 | 3/1998 |
| CN | 1208539 | 1/1999 |
| EP | 0 234 733 B1 | 11/1991 |
| EP | 0 713 653 A1 | 5/1996 |
| EP | 1 894 472 | 10/1997 |
| EP | 0 965 578 | 12/1999 |
| EP | 1 239 022 | 9/2002 |
| EP | 1 419 768 | 5/2004 |
| GB | 0111282.0 | 5/2001 |
| JP | S63297342 A | 12/1988 |
| JP | 06256179 A | 9/1994 |
| JP | 8-143454 | 6/1996 |
| JP | 08214891 | 8/1996 |
| JP | 8-511533 | 12/1996 |
| JP | 09-023817 | 1/1997 |
| JP | 09030962 A | 2/1997 |
| JP | 10-101568 | 4/1998 |
| JP | 10-155459 | 6/1998 |
| JP | 10-191886 | 7/1998 |
| JP | 11034236 A | 2/1999 |
| JP | 2000-8074 | 1/2000 |
| JP | 2000-516261 | 12/2000 |
| JP | 2001-31586 A | 2/2001 |
| JP | 2003-48831 | 2/2003 |
| JP | 2003-504333 | 2/2003 |
| JP | 2003-113120 | 4/2003 |
| JP | 2005132758 A | 5/2005 |
| JP | 2006-502196 | 1/2006 |
| JP | 2006/076948 A | 3/2006 |
| JP | 2006-83134 | 3/2006 |
| JP | 2006-83136 | 3/2006 |
| JP | 2006-521369 | 9/2006 |
| JP | 2007-008863 | 1/2007 |
| WO | 94/28913 | 12/1994 |
| WO | WO 94/28891 | 12/1994 |
| WO | 96/10922 | 4/1996 |
| WO | WO 96/21037 | 7/1996 |

(Continued)

OTHER PUBLICATIONS

GlaxoWellcome; "Zung Self-Rating Depression Scale" 1997.*

(Continued)

*Primary Examiner* — Susan Hoffman
(74) *Attorney, Agent, or Firm* — Drinker Biddle & Reath LLP

(57) ABSTRACT

A composition having an activity of ameliorating the reduced amount of diurnal activity and/or depressive symptoms, comprising arachidonic acid and/or a compound having arachidonic acid as a constituent fatty acid.

15 Claims, 3 Drawing Sheets

(56) References Cited

FOREIGN PATENT DOCUMENTS

| WO | WO-9640106 A2 | 12/1996 |
|---|---|---|
| WO | WO-9726804 A1 | 7/1997 |
| WO | WO-9808501 A1 | 3/1998 |
| WO | 98/50052 | 11/1998 |
| WO | WO 00/21524 | 4/2000 |
| WO | 01/03696 | 1/2001 |
| WO | WO-0124645 A1 | 4/2001 |
| WO | 01/85158 A2 | 11/2001 |
| WO | WO-0184961 A2 | 11/2001 |
| WO | 01/91745 A2 | 12/2001 |
| WO | WO 01/97793 A2 | 12/2001 |
| WO | 02/02105 | 1/2002 |
| WO | WO 02/19839 | 3/2002 |
| WO | 02/089787 A1 | 11/2002 |
| WO | 02/102394 A2 | 12/2002 |
| WO | 03/004667 | 1/2003 |
| WO | 03/013497 A1 | 2/2003 |
| WO | WO-03013497 A1 | 2/2003 |
| WO | 03/092673 A1 | 11/2003 |
| WO | 2004/024930 A2 | 3/2004 |
| WO | WO 2004/024136 A1 | 3/2004 |
| WO | 2004/028529 | 4/2004 |
| WO | 2004/084882 | 10/2004 |
| WO | 2004/091663 A1 | 10/2004 |
| WO | 2005/018632 | 3/2005 |
| WO | WO 2005/037848 A2 | 4/2005 |
| WO | 2005/072306 | 8/2005 |
| WO | 2006/030552 | 3/2006 |

OTHER PUBLICATIONS

Louis-Joseph Auguste et al., Prevention of Stress-Induced Enteral Nutrition, vol. 14, No. 6, 1990, pp. 615-617.

Search Report dated Jul. 20, 2005 for International Patent Application No. PCT/JP2005/005622 filed Mar. 18, 2005.

John R. Burgess et al.; "Long-Chain Polyunsaturated Fatty Acids in Children With Attention-Deficit Hyperactivity Disorder"; American Journal of Clinical Nutrition, Bethesda, MD, US, vol. 71, No. 1, Suppl, Jan. 2000, pp. 237S-330S; XP008000462.

Search Report dated Jul. 11, 2005 from International PCT Application No. PCT/JP2005/005623.

Susumu Kotani et al., "Dietary supplementation of arachidonic and docosahexanoic acids improves cognitive dysfunction," 2006, pp. 159-164, vol. 56, Neuroscience Research, Limerick, Ireland.

Search Report dated Mar. 4, 2008 for International Application No. PCT/JP2007/075403 filed Dec. 27, 2007.

Yoshimura et al., "FGF-2 regulation of neurogenesis in adult hippocampus after brain injury," PNAS, May 8, 2001, vol. 98, No. 10, pp. 5874-5879.

Nakatomi et al., "Regeneration of Hippocampal Pyramidal Neurons after Ischemic Brain Injury by Recruitment of Endogenous Neural Progenitors," Cell, vol. 110, Aug. 23, 2002, pp. 429-441.

Kawakita et al., "Docosahexaenoic Acid Promotes Neurogenesis in Vitro and in Vivo," Neuroscience, 2006, vol. 139, pp. 991-997.

Hirano et al., "Influence of Taurine Load on Neural Development," Program of the 173rd Meeting of the Essential Amino Acid Research Council, 2003, p. 1 (with partial English-language translation).

European Search Report dated Jan. 27, 2010 in EP Application No. 07860598.7.

Search Report dated Jan. 31, 2007 for International Application No. PCT/JP2006/313437 filed Jun. 29, 2006.

Database WPI Week 200064, Derwent Publications Ltd., London, GB; AN 2000-658544, XP002410776.

Choi-Kwon, Smi et al., "Temporal changes in cerebral antioxidant enzyme activities after ischemia and reperfusion in a rat focal brain ischemia model: effect of dietary fish oil," Developmental Brain Research, Aug. 18, 2004, pp. 11-18, vol. 152, No. 1, XP007901417.

Supplementary European Search Report dated Aug. 30, 2010, issued in European patent application No. 04 74 3331.

Kark et al., "Adipose Tissue n-6 Fatty Acids and Acute Myocardial Infarction in a Population Consuming a Diet High in Polyunsaturated Fatty Acids", *Am J Clin Nutr*, 77, 796-802 (2003).

McNamara et al., "The Neuropharmacological and Neurochemical Basis of Place Learning in the Morris Water Water Maze," Brain Res. Rev., vol. 18, pp. 33-49 (1993).

Reddy, "Preclinical and Clincal Behavioral Paradigms for Testing Drugs that Affect Learning and Memory Processes," Methods Find. Exp. Clin. Pharmacol. vol. 20, No. 3, pp. 249-277 (1998).

McGahon et al., "Age-Related Changes in Synaptic Function: Analysis of the Effect of Dietary Supplementation with ω-3 Fatty Acids," Neuroscience, vol. 94, No. 1, 1999, pp. 305-314.

Office Action dated Jun. 28, 2010 in European Patent Application 03 748 553.9.

Gorelick et al., "Stroke Prevention Therapy Beyond Antithrombotics: Unifying Mechanisms in Ischemic Stroke Pathogenesis and Implications for Therapy: An Invited Review," Stroke; pp. 862-875, 2002. vol. 33.

Science Daily, "Brain Atrophy in Elderly Leads to Unintended Racism, Depression and Problem Gambling," Association for Psychological Sciences, 2007.

Yuksel et al., "Evaluation of mental retardation—Part 1: Etiologic classification of 4659 patients with mental retardation or multiple congenital abnormality and mental retardation," J. Pediatr. Neurosci, vol. 2, (2007), pp. 45-52.

Office Action dated Sep. 3, 2010 in Russian Patent Application No. 2008103361/15(003664) (with English translation).

Psychiatry edited by R. Sheider, Moscow, Praktika, 1998, pp. 280-282 and 287-289 (with English Translation).

The Merck Manual, Fifteenth Edition 1987, pp. 1421-1424.

Simopoulos, "Essential fatty acids in health and chronic disease," Am. J. Clin, Nutr, (1999), vol. 70, pp. 560S-569S.

Happe et al., "Time to give up on a single explanation for autism," Nature Neuroscience, vol. 9, No. 10, Oct. 2006, pp. 1218-1220.

Vericel et al., "The influence of low intake of η-3 fatty acids on platelets in elderly people," Atherosclerosis, vol. 147, (1999) pp. 187-192.

Nakawatase et al., "Alzheimer's Disease and Related Ementias," Cecil's Textbook of Medicine (Twenty-First Edition, vol. 1), W.B. Saunders Company, 2000, pp. 2042-2045.

Hart et al. "The Contribution of Risk Factors to Stroke Differentials, by Socioeconomic Position in Adulthood: The Renfrew/Paisley Study," Am. J. of Public Health, vol. 90, No. 11 (Nov. 2000), pp. 1788-1791.

Belmonte et al., "Fragile X syndrome and autism at the intersection of genetic and neural networks," Nat. Neurosci., vol. 9, No. 10 (Oct. 2006), pp. 1221-1225.

Office Action dated Jun. 8, 2010 in Japanese Patent Application JP2004-539481 (in Japanese).

Kelley et al., "Arachidonic Acid Supplementation Enhances Synthesis of Eicosanoids Without Suppressing Immune Functions in Young Healthy Men," Lipids, vol. 33, No. 2 (1998) pp. 125-130.

Lynch et al., "Impaired Spatial Memory in Aged Rates is Associated with Alterations in Inositol Phospholipid Metabolism," NeuroReport, vol. 5, 1994, pp. 1493-1497, Lippincott Williams & Wilkins, London, England.

Wainwright et al., "Water Maze Performance is Unaffected in Artificially Reared Rats Fed Diets Supplemented with Arachidonic Acid and Docosahexaenoic Acid," J. Nutr., vol. 129, 1999, pp. 1079-1089, American Society for Nutritional Sciences, Bethesda, MD.

Wainwright et al., Arachidonic Acid Offsets the Effects on Mouse Brain and Behavior of a Diet with a Low (n-6):(n-3) Ratio and Very High Levels of Docosahexaenoic Acid, J. Nutr., vol. 127, 1997, pp. 184-193, American Society for Nutritional Sciences, Bethesda, MD.

Youdim et al., "Essential Fatty Acids and the Brain: Possible Health Implications," Int. J. Dev. Neurosci., vol. 18, 2000, pp. 383-399, Oxford Elsevier Science, New York, NY (Abstract Only).

Kawashima et al., "Enzymatic Synthesis of High-Purity Structured Lipids with Caprylic Acid at 1,3-Positions and Polyunsaturated Fatty Acid at 2-Position," J. Am. Oil Chem. Soc., vol. 78, 2001, pp. 611-616, American Oil Chemists Society, Champaign, IL.

(56) References Cited

OTHER PUBLICATIONS

Mackay & Mochly-Rosen, "Arachidonic Acid Protects Neonatal Rat Cardiac Myocytes from Ischaemic Injury though ε Protein Kinase C," Cardiovascular Res. vol. 50, 2001, pp. 65-74, Elsevier Science B.V., Amsterdam, Holland.
Horrobin, "Abnormal Membrane Concentrations of 20 and 22-Carbon Essential Fatty Acids: A Common Link Between Risk Factors and Coronary and Peripheral Vascular Disease," Prostaglandins Leukot. Essent. Fatty Acids, vol. 53, 1995, pp. 385-396, Churchill Livingstone, Edinburgh, Scotland.
Webster's Third New International Dictionary, 1963, p. 1798, G.& C. Merriam Co., Springfield, MA.
Strub, "Vascular Dementia," South. Med. J., vol. 96, 2003, pp. 363-366, Southern Medical Association, Birmingham, AL.
McGahon et al., "The Ability of Aged Rats to Sustain Long-Term Potentiation is Restored When the Age-Related Decrease in Membrane Arachidonic Acid Concentration is Reversed"; Neuroscience, vol. 81, (1997), pp. 9-16.
Koletzko et al., "Polyunsaturated fatty acids in human milk and their role in early infant development," Journal of Mammary Gland Biology and Neoplasia, Jul. 1999, pp. 269-294, vol. 4, No. 3.
Carlson S.E., "Docosahexaenoic acid and arachidonic acid in infant development," Seminars in Neonatology, Oct. 2001, pp. 437-449, vol. 6, No. 5.
Auestad et al., "Visual, cognitive, and language assessments at 39 months: a follow-up study of children fed formulas containing long-chain polyunsaturated fatty acids to 1 year of age," Pediatrics, Sep. 2003, pp. e177-e183, vol. 112, No. 3, Pt 1.
Willatts et al., "Effect of Long-Chain Polyunsaturated Fatty Acids in Infant Formula on Problem Solving at 10 Months of Age," Lancet, vol. 352, 1998, 688-691, Lancet, Publishing Group, London, England.
Lucas et al., "Efficacy and safety of long-chain polyunsaturated fatty acid supplementation of infant-formula milk: a randomized trial," LANCET, Dec. 4, 1999, pp. 1948-1954, vol. 354 No. 9194.
Office Action dated Oct. 16, 2008 in Canadian Patent Application No. 2,456,049.
Office Action dated Mar. 2, 2010 in Japanese Patent Application No. 2004-539481 (In Japanese).
Kotani et al. "Improvement of Synaptic plasticity in the hippocampus of aged rats by ingestion of arachidonic acid," 24$^{th}$ Japan Neurosurigical Society Program, (2001), p. 243. (In Japanese w/English translation).
Office Action issued Jan. 4, 2011, in Japanese Patent Application No. 2009-147715 (in Japanese).
Novel Food Information—DHASCO® and ARASCO® from Health Canada, Date Modified Jan. 31, 2003.
Song et al., "Effects of dietary n-3 or n-6 fatty acids on interleukin-1β-induced anxiety, stress, and inflammatory responses in rats," J. Lipid Res. Oct. 2003, vol. 44, No. 10, pp. 1984-1991 (electronically published Jul. 1, 2003).
Mills et al., "Psychosocial stress, catecholamines, and essential fatty acid metabolism in rats," Proc. Soc. Exp. Biol. Med. Jan. 1994, vol. 205, No. 1, pp. 56-61.
Office Action dated Jan. 18, 2011 issued in Japanese Patent Application. No. 2004-271927 (In Japanese).
Kawashima et al., "Enzymatic Synthesis of High-Purity Structured Lipids with Caprylic Acid at 1,3-Positions and Polyunsaturated Fatty Acid at 2-Position," JAOCS, vol. 78, No. 6 (2001).
Office Action dated Jan. 11, 2011 issued in Japanese Patent Application. No. 2001-235519 (In Japanese).
Wollan et al., "Dietary essential fatty acids and gender-specific difference in rat maze learning and memory," Neuroscience Abstract, 2000, No. 793.13, Society for Neuroscience, vol. 26.
D.A. Kharkevich, Farmakologiya [Pharmacology], M., Meditsina, 1987, pp. 41-42. (In Russian).
V.G. Belikov, Farmatsevticheskaya khimiya, [Pharmaceutical Chemistry], M., Vysshaya shkola, 1993, vol. 1, pp. 43-47. (In Russian).
Written Opinion mailed Nov. 7, 2006 in International PCT Application PCT/JP2006/313444 filed Jun. 29, 2006.

Office Action mailed Jan. 26, 2010 in Russian Application No. 2008103361/15(003664) with English language translation.
Search Report dated Nov. 7, 2006 for International Application No. PCT/JP2006/313444 filed Jun. 29, 2006.
Taiwanese Office Action issued Mar. 24, 2011 in Taiwanese Patent Application No. 092126198 (in Chinese).
European Office Action issued May 2, 2011 in European Patent Application No. 06780813.9.
Ulmann et al., "Brain and hippocampus fatty acid composition in phospholipid classes of aged-relative cognitive deficit rats," Prostaglandins, Leukotrienes and Essential Fatty Acids, vol. 64, Issue 3, Mar. 2001 (abstract).
The Merck Manual of Diagnosis and Therapy, 18th Ed., Merck Research Laboratories, 2006, pp. 1816-1818.
Japanese Office Action issued Jul. 19, 2011 in JP 2005-191506 (in Japanese).
K. Naliwaiko et al., "Effects of Fish Oil on the Central Nervous System: A New Potential Antidepressant?," Nutritional Neuroscience, vol. 7, No. 2, pp. 91-99 (2004).
Golfetto et al., Nutr. Neurosci., 2001, 4(1), 75-79, abstract.
Japanese Office Action dated Jul. 12, 2011 issued in JP Application No. 2004-271958.
Yakkyoku (Pharmacy), 2000, vol. 51, No. 2, p. 2-10 (w/partial English Translation).
Modern Physician, 2002, vol. 22, No. 9, p. 1155-1157 (w/partial English translation).
Japanese Office Action dated Aug. 9, 2011 issued in JP Application No. 2005-191624.
M. Minami et al., "Dietary Docosahexaenoic Acid Increases Cerebral Acetylcholine Levels and Improves Passive Avoidance performance in Stroke-Prone Spontaneously Hypertensive Rats" Pharmacology Biochemistry and Behavior, vol. 58, No. 4, pp. 1123-1129 (1997).
Russian Office Action issued Sep. 14, 2011 in Russian Application No. 2008103361/15(003664) (w/ English translation).
Bolshaya Rossijskaya Entsyclopediya, 1992, vol. 3, p. 202 (w/ English translation).
Office Action issued Feb. 17, 2011 in Chinese Patent Application No. 200480001751.X (with English translation).
Korean Office Action ussed Sep. 27, 2011 in Korean patent application No. 7005102/2005 (w/English translation).
Gordon, "Nutrition and cognitive function," Brain & Development 19 (1997) pp. 165-170.
Office Action dated Sep. 22, 2011 issued in Australian Patent Application No. 2005283697.
Stevens et al., "EFA Supplementation in Children with Inattention, Hyperactiveity, and Other Distruptivce Behaviors," Lipids, vol. 38, No. 10, (2003), pp. 1007-1021.
Lynch, "Analysis of the Mechanisms Underlying the Age-related Impairment in Long-Term Potentiation in the Rat," Reviews in the Neurosciences, vol. 9, pp. 169-201 (1998).
Anderson et al. "Breast Feeding and cognitive development: a meta-analysis," Am. J. Clin. Nutr., vol. 70, pp. 525-535, (1999).
Crawford, "The role of essential fatty acids in neural development: implications for perinatal nutrition." Am. J. Clin. Nutr., pp. 703S-710S, vol. 57 (suppl) (1993).
Crawford et al., "Are deficirs of arachidonic and docosahexaenoic acids responsible for the neural and vascular complications of preterm babies?," Am. J. Clin. Nutr., vol. 66 (suppl), pp. 1032S-1041S (1997).
Hempenius et al., "Preliminary Safety assessment of an Arachidonic Acid-enriches Oil derived from Mortierella alpina: Summary of Toxicological Data," Food and Chemical Toxicology, vol. 35, pp. 573-581 (1997).
Birch et al., "A randomized controlled trial of early dietary supply of long-chain polyunsaturated fatty acids and mental development in term infants," Developmental Medicine & Child Neurology, vol. 42, pp. 174-181 (2000).
Kalmijn et al., "Dietary Fat Intake and the Risk of Incident Dementia in the Rotterdam Study," Annals of Neurology, pp. 776-782 (1997).
Soderberg et al., "Fatty Acid Composition of Brain Phospholipids in Aging and in Alzheimer's Disease," Lipids, vol. 26, No. 6, pp. 421-425 (1991).

(56) References Cited

OTHER PUBLICATIONS

Ferguson, Letter to Linda Kahl, Ph.D., Aug. 3, 2011, "Re: GRAS Notice for ARASCO® (arachidonic acid-rich single-cell oil) Level in Term Infant Formula."

Wieraszko, "Avian Hippocampus as a model to Study Spatial Orentation-Related Synaptic Plasticity," Molecular and Cellular Mechanisms of Neuronal Plasticity, pp. 107-129 (1998).

Notice of Opposition against EP1419768 by Abbott Laboratories (May 17, 2012).

Notice of Opposition against EP 1419768 by N.V. Nutricia (May 16, 2012).

Fields, Letter to Food and Drug Administration, Aug. 27, 1998, "Re: Notice of a Claim for Exemption From Premarket Approval," avaliable at http://www.accessdata.fda.gov/scripts/fch/gras_notices/grn_7.pdf, documents created in 1998.

Randolph, "Repetable Battery for Assessment of Neuropsychological Status (RBANSTM)," avaliable at http://www.pearsonassessments.com/HAIWEB/Cultures/en-us/Productdetail.htm?Pid=015-8166-000 (last visited Jul. 3, 2012).

Chinese Office Action dated Apr. 28, 2013 issued in Chinese Patent Application No. 200610100093.0 (In Chinese).

Aronen et al., "Motor activity and severity of depression in hospitalized prepubertal children," J Am Acad Child Adolesc Psychiatry, Jun. 1996;35(6):752-63.

Notice of Opposition against EP 1542670 filed by N.V. Nutricia (Feb. 27, 2014).

McGahon, et al., "Age-related changes in oxidative mechanisms and LTP are reversed by dietary manipulation", Neurobiology of Aging 20 (1999) pp. 643-653.

McGahon, et al., "Training in the Morris Water Maze Occludes the Synergism Between ACPD and Arachldonic Acid on Glutamate Release in Synaptosomes Prepared from Rat Hippocampus", Learning Memory 1996 3: 296-304.

Kotani et al., "Diet of Arachidonic Acid Improved Synaptic Plasticity in Aged Rat Hippocampal CA1 Neuron", Neuroscience, 316.13, Nov. 12, 2001 (Abstract).

Beukers, et al., "Pharmacology of long-term potentiation—A model for learning reviewed", Pharm Weekbl[Sci] 1991: 13(1). pp. 7-12.

Horimoto, et al., "Arachidonic acid Activation of Potassium Channels in Rat Visual Cortex Neurons", Neuroscience, 1997. vol. 77, No. 3, pp. 661-671.

Bach, et al., "Medium-chain triglycerides: an update", The American Journal of Clinical Nutrition 36: Nov. 1982, pp. 950-962.

Japanese Office Action dated Jun. 4, 2013 in Japanese Patent Application No. 2011-230136 (in Japanese).

Fijita et al., "Docosahexaenoic acid Improves long-term potentation attenuated by phospholipase A(2) inhibitor in rat hippocampal slices," Br. J. Pharmacol. 132(7):1417-22 (2001).

Danysz et al., "The NMDA receptor antagonist memantine as a symptomatological and neuroprotective treatment for Alzheimes's disease: preclinical evidence," Int. J. Geriatr. Psychiatry (Suppl 1) S23-32 (2003).

Japanese Office Action issued May 20, 2014 in JP 2005-191624 (in Japanese).

Yamashima et al., "Evaluation of hight-order brain function by RBANS neuropsychological test," Brain and Nerve, 54(6): 463-471 (2002) (with partial English translation).

Decision Revoking the European Patent mailed Nov. 25, 2014, in EP Patent No. 1 419 768 B1.

Umeda-Sawada et al., "Distribution and Metabolism of Dihomo-γ-linolenic Acid (DGLA, 20:3n-6) by Oral Supplementation in Rats", Biosci. Biotechnol. Biochem., 2006, 70 (9), 2121-2130.

Wang, et al., "The flavonoid baicalein promotes NMDA receptor-dependent long-term porentation and enhances memory", British Journal of Pharmacology, 2011, 162, 1364-1379.

Park, et al., "Mismatch between changes in baicaleln-induced memory-related biochemical parameters and behavioral consequences in mouse", Brain Research, 2010, 1355, 141-150.

Casey, et al., "Analysis of the Presynaptic Signaling Mechanisms Underlying the Inhibition of LTP in Rat Dentate Gyrus by the Tyrosine Kinase Inhibitor, Genistein", Hippocampus, 2002, 12:377-385.

Huang, et al., "Genistein reduced the neural apoptosis in the brain ovariectomised rats by modulating mitochondrial oxidative stress", British Journal of Nutrition, 2010, 104, 1297-1303.

Lathe, "Hormones and the hippocampus", Journal of Endocrinology, 2001, 169, 205-231.

Llenalla Garcia Fernández, "Statistical Issues for Patent Specification EP 1 419 768 B1", Jun. 2013.

Gitto, et al., "The patient with Alzheimer's disease", Quintessence International, Nov. 3, 2001, 32:221-231.

P. Srinivas, "Diagnosis and Management of Alzheimer's Disease—An Update", Med J Malaysia, Dec. 1999, vol. 54, No. 4, pp. 541-550.

CNS Neutotransmitters & Neuromodulators: Acetycholine, 1994, ed. Trevor W. Stone, pp. 39-47 (Monferini, "Subtypes of Neuronal Muscarinic Receptors: Pharmacological Criteria"); p. 204.

Bliss, et al., "A synaptic model of memory: long-term potentiation in the hippocampus", Nature, Jan. 7, 1993, 361:31-39.

Marlinez, et al., "Long-Term Potentiation and Learning", Annu. Rev. Psychol, 1996, 47:173-203.

Will Block, "Protect Brain Function by Enhancing Vascular Health," Aug. 2001, available at http://www.life-enhancement.com/magazine/article/594-protect-brain-function-by-enhancing-vascular-health.

* cited by examiner

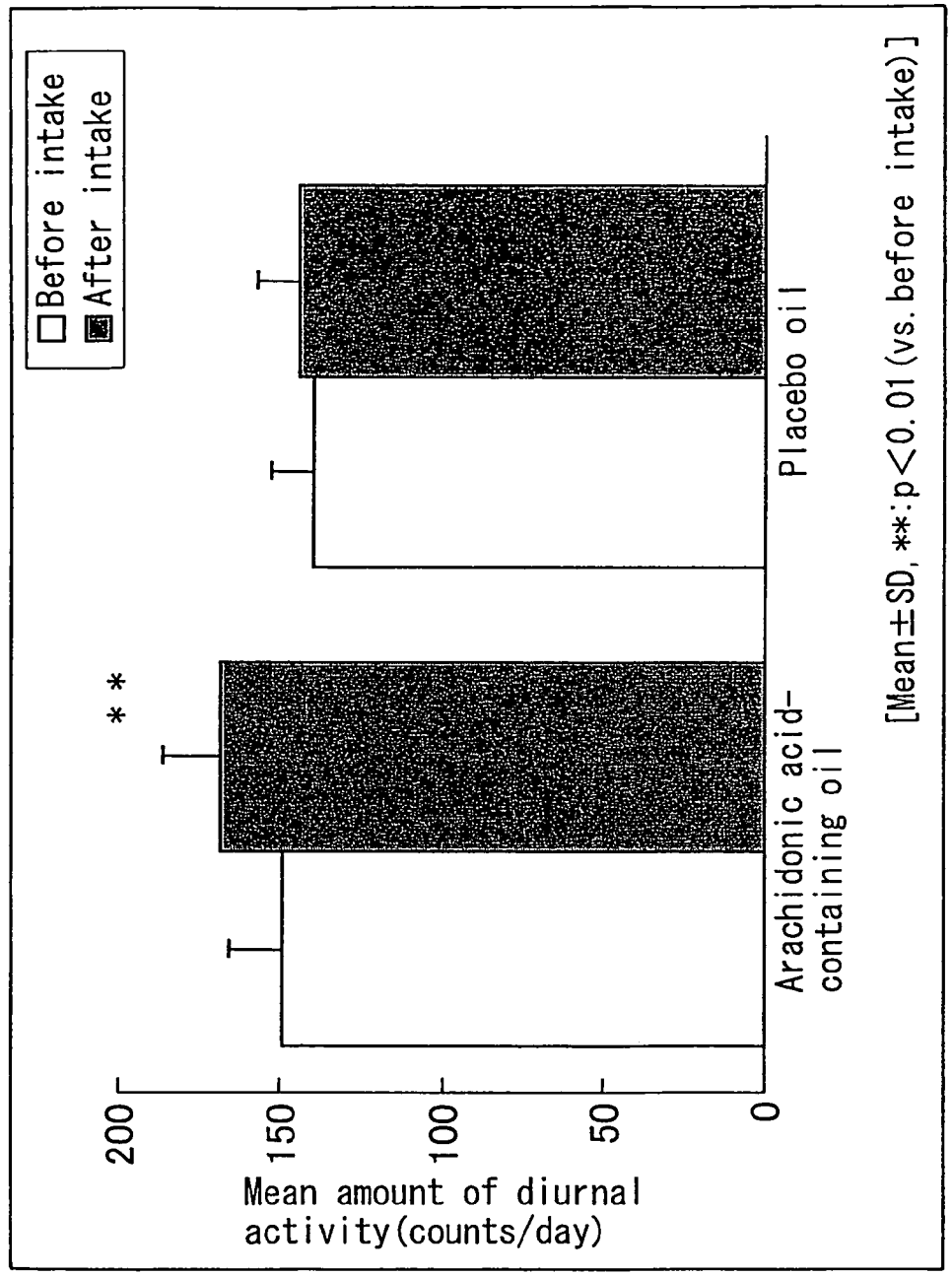

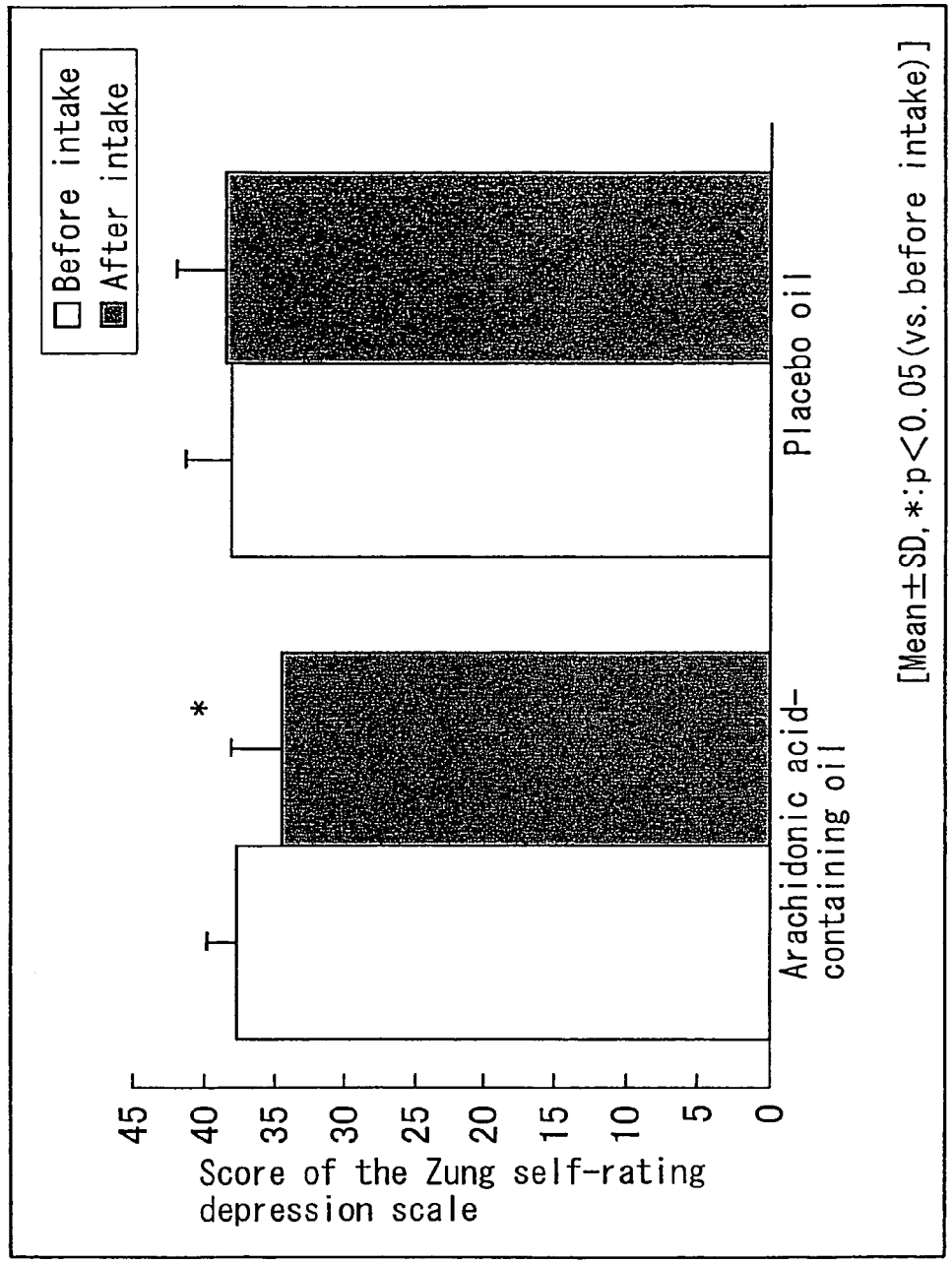

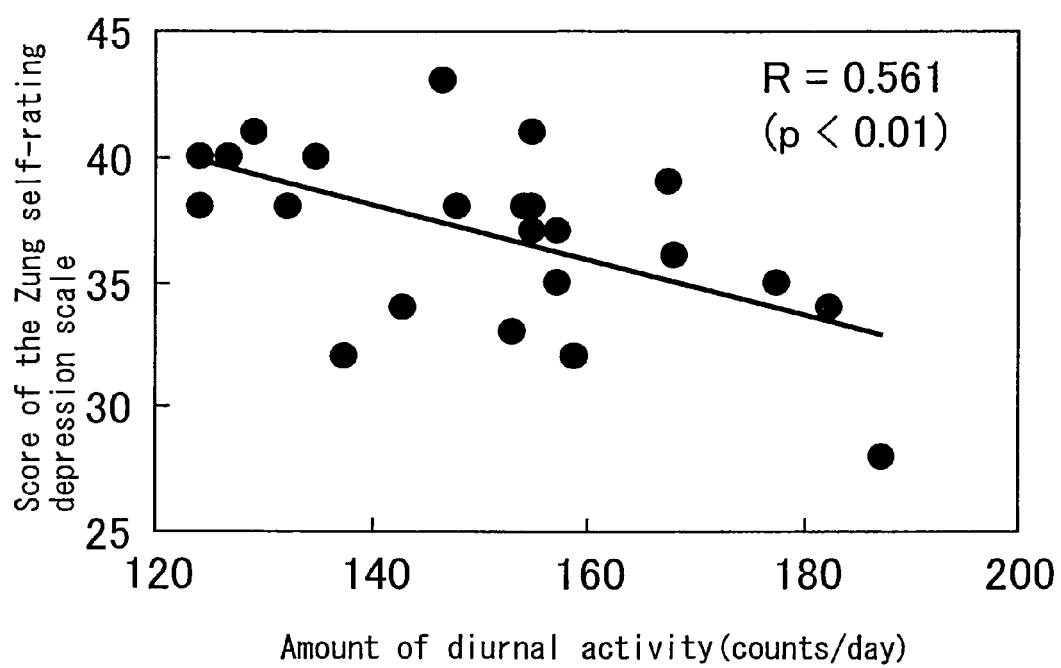

COMPOSITIONS AMELIORATING A REDUCED DIURNAL ACTIVITY AND/OR DEPRESSIVE SYMPTOMS

CROSS REFERENCE TO RELATED APPLICATIONS

This application is the National Stage of International Application No. PCT/JP2006/313444 filed Jun. 29, 2006, which claims benefit of Japanese Patent Application No. 2005-191506 filed on Jun. 30, 2005, and which are incorporated by reference herein in their entirety.

TECHNICAL FIELD

The present invention relates to a composition having an activity of ameliorating a reduced amount of diurnal activity and/or depressive symptoms.

BACKGROUND ART

It is well known that a reduced amount of diurnal activity and depressive symptoms may be noted in elderly people. There is a report that the amount of diurnal activity is closely related to sleep, and sleep disorders may often reduce the amount of diurnal activity, and the amount of diurnal activity correlates with the quality and the quantity of sleep at night [Psychiatry Clin Neurosci Vol. 54, 309-310 (2000)]. The incidence of sleep disorders markedly increases with aging. In the background of the increased incidence of sleep disorders in the elderly people, there are often age-related changes in sleep as represented by increased cases of arousal during sleep, difficulty in resuming sleep after arousal, curtailment in total sleeping hours, reduced sleep efficiency, and reduced slow wave sleep. Overlapping these physiological changes, it is believed, a great variety of sleep-interrupting factors may occur which results in the onset of sleep disorders of the elderly [Medical Frontier (Saisin Igaku) Vol. 59, 468-475 (2004)].

On the other hand, a variety of mental disorders are believed to induce the reduced amount of diurnal activity and/or depressive symptoms directly or via symptoms such as sleep disorders. For example, in patients with schizophrenia, there are known not only insomnia resulting from difficulty in sleeping and from arousal during sleep but also sleep disorders resulting from disturbances in the sleep and the waking rhythm such as changes in life patters and irregular daily lives. Among mental disorders, emotional disturbance is frequently accompanied by sleep disorders and depressive symptoms: unipolar depression exhibits insomniac symptoms such as difficulty in sleeping, arousal during sleep, early morning arousal, lack of sensation of deep sleep, and curtailment of sleeping hours, and the bipolar depression exhibits insomniac symptoms similar to those in the unipolar depression, but in the bipolar depression unlike the unipolar depression, hypersomnia such as repeated napping is often noted. In addition, neurological disorders also cause sleep disorders and depressive symptoms, and as neurological disorders that are often accompanied by sleep disorders, there can be mentioned cerebral degenerative disorders, dementia, Parkinson's disease, lethal familial insomnia, sleep-related epilepsy, epileptic seizure wave state during sleep, sleep-related headache and the like [Supplement, Nippon Rinsho (Japanese Journal of Clinical Medicine) Vol. 39, 231-248 (2003)].

In recent years, methods of using an actigraph are attracting attention as methods of evaluating the quality of sleep and the amount of activity. The actigraph is a wristwatch-type device that has built in a sensor for measuring the amount of activity and is worn on the nondominant arm to measure the amount of activity night and day with one week as a unit thereby to assess changes in the amount of activity. Analyzing the result of this actigraph measurement, by computer software, is believed, to be very useful for diagnosing, observing the progress of, and judging the therapeutic effects of sleep disorders, the reduced amount of activity etc. associated with mental diseases, neurological diseases and aging.

As therapeutic methods for the reduced amount of diurnal activity and depressive symptoms due to such sleep disorders and reduced mental and physical functions, there are psychotherapeutic approaches, non-drug therapies, and drug therapies. Non-drug therapies include high illumination radiation, which is now aggressively used in the treatment of seasonal emotional disturbance and circadian rhythm sleep disorders. Though vitamin $B_{12}$ and benzodiazepine hypnotics etc. are being used as drug therapies for the treatment of sleep disorders and depressive symptoms, none of them can be said to be very effective, and the establishment of drug therapies is being awaited. For the treatment of emotional disturbance and neurological diseases, it is common to combine antidepressants and psychotropic drugs with hypnotics. However, there are currently no safe and effective compounds that have therapeutic effects for the treatment of the reduced amount of diurnal activity and depressive symptoms due to sleep disorders and reduced mental and physical functions.

As a compound that controls sleep and behavior, cannabinoids are known. Cannabinoids are reported to affect memory and learning [Nature Vol. 388, 773-778 (1997)] and eating, relaxation and sleep [J Neurosci Vol. 21, 5344-5350 (2001)] via cannabinoid receptors in the brain. As endogenous cannabinoids in the human body, arachidonic acid-containing compounds, such as anandamide and 2-arachidonoyl monoglycerol, are known. These cannabinoids, even when orally ingested, undergo hydrolysis and thus are not absorbed as they are. Reports on them so far only describe in vitro experiments or experiments on the administration of receptor inhibitors.

Thus, it was not clear at all whether compounds containing arachidonic acid as a constituent fatty acid ingested by humans affect the reduced amount of diurnal activity and depressive symptoms.

Non-patent document 1: Psychiatry Clin Neurosci Vol. 54, 309-310 (2000)
Non-patent document 2: Medical Frontier (Saisin Igaku) Vol. 59, 468-475 (2004)
Non-patent document 3: Supplement, Nippon Rinsho (Japanese Journal of Clinical Medicine) Vol. 39, 231-248 (2003)
Non-patent document 4: Nature Vol. 388, 773-778 (1997)
Non-patent document 5: J Neurosci Vol. 21, 5344-5350 (2001)

DISCLOSURE OF THE INVENTION

Thus, it is an object of the present invention to provide a food and a drink that have an activity of ameliorating the reduced amount of diurnal activity and/or depressive symptoms, said food and drink comprising arachidonic acid and/or a compound which has an arachidonic acid as a constituent fatty acid, and methods of producing them. More specifically, it is an object of the present invention to provide a food and a drink that have an activity of ameliorating the reduced amount of diurnal activity and/or depressive symptoms resulting from sleep disorders that are caused by mental diseases (schizophrenia, depression etc.), neurological diseases (cerebral degenerative diseases, dementia, Parkinson's disease, lethal familial insomnia, sleep-related epilepsy, epileptic seizure wave state during sleep, sleep-related headache, etc.), or an aging-related reduction in mental and physical functions, said food and drink comprising, as an active ingredient, at least one selected from the group consisting of: arachidonic acid; an alcohol ester of arachidonic acid; and a triglyceride, a phospholipid and a glycolipid wherein part or all of the constituent fatty acids is arachidonic acid, and a method of producing them.

After intensive and extensive research to elucidate the effect of ameliorating the reduced amount of diurnal activity and depressive symptoms of an agent comprising, as an active ingredient, arachidonic acid and/or a compound which has an arachidonic acid as a constituent fatty acid, the present inventors have surprisingly demonstrated the effect of a compound comprising arachidonic acid as an active ingredient for ameliorating the reduced amount of diurnal activity and depressive symptoms of elderly people who are staying, for a short period, in an aged care facility by evaluating using the values measured by an actigraph as an index.

Thus, the present invention provides an ameliorating agent for the reduced amount of diurnal activity and/or depressive symptoms, said agent comprising as an active ingredient arachidonic acid and/or a compound having arachidonic acid as a constituent fatty acid, as well as a composition having an effect of ameliorating the reduced amount of diurnal activity and/or depressive symptoms and a method of producing the composition. More specifically, the present invention provides an ameliorating agent for the reduced amount of diurnal activity and/or depressive symptoms resulting from sleep disorders that are caused by mental diseases (schizophrenia, depression etc.), neurological diseases (cerebral degenerative diseases, dementia, Parkinson's disease, lethal familial insomnia, sleep-related epilepsy, epileptic seizure wave state during sleep, sleep-related headache, etc.), and the reduced amount of diurnal activity and/or depressive symptoms resulting from sleep disorders due to an aging-related reduction in mental and physical functions, said agent comprising, as an active ingredient, at least one selected from the group consisting of: arachidonic acid; an alcohol ester of arachidonic acid; and a triglyceride, a phospholipid and a glycolipid wherein part or all of the constituent fatty acids is arachidonic acid, and a method of producing them, as well as a composition having the preventing or ameliorating effect and a method of producing the composition.

BRIEF EXPLANATION OF THE DRAWINGS

FIG. 1 is a drawing that shows the effect of an arachidonic acid-containing oil on the amount of diurnal activity of the elderly persons evaluated using an actigraph.

FIG. 2 is a drawing that shows the effect of an arachidonic acid-containing oil on the depressive symptoms of the elderly persons evaluated using the scoring of the Zung self-rating depression scale.

FIG. 3 is a drawing that shows the correlation of the amount of diurnal activity of the elderly persons who ingested an arachidonic acid-containing oil and the score by the scoring of the Zung self-rating depression scale.

BEST MODE FOR CARRYING OUT THE INVENTION

The present invention relates to an ameliorating agent for a reduced amount of diurnal activity and/or depressive symptoms, said agent comprising, as an active ingredient, arachidonic acid or an arachidonic acid-containing oil, as well as a composition having an effect of preventing or ameliorating the reduced amount of diurnal activity and/or depressive symptoms, and a method of producing the composition.

As causes of the reduced amount of diurnal activity and/or depressive symptoms, there can be mentioned sleep disorders due to mental diseases (schizophrenia, depression etc.), sleep disorders due to neurological diseases (cerebral degenerative diseases, dementia, Parkinson's disease, lethal familial insomnia, sleep-related epilepsy, epileptic seizure wave state during sleep, sleep-related headache, etc.), or sleep disorders due to aging-related reduction in mental and physical functions. These symptoms or diseases are not limiting, however, and all symptoms or diseases that are related to the reduced amount of diurnal activity and/or depressive symptoms are included.

The active ingredient of the present invention is arachidonic acid, and all compounds having arachidonic acid as a constituent fatty acid can be used. Compounds having arachidonic acid as a constituent fatty acid include, for example, arachidonic acid salts such as a calcium salt and a sodium salt. Lower alcohol esters of arachidonic acid include, for example, an arachidonic acid methyl ester and an arachidonic acid ethyl ester. Also, there can be used triglycerides, phospholipids, glycolipids etc. in which part or all of the constituent fatty acids is arachidonic acid. The present invention is not limited to those listed above, and all compounds having arachidonic acid as the constituent fatty acid may be used.

When an application into foods is contemplated, arachidonic acid is preferably in the form of a phospholipid, specifically a triglyceride. There are no or few natural sources for arachidonic acid-containing triglycerides (synonymous with triglycerides containing triglycerides in which part of all of the constituent fatty acids is arachidonic acid). The present inventors have realized the industrial use of triglycerides containing arachidonic acid as a constituent fatty acid, which was subjected to an ingestion study for the reduced amount of diurnal activity and/or depressive symptoms of the elderly, and have demonstrated, for the first time, the effect of the active ingredient of the present invention in tests on humans, and have revealed that it has an effect of preventing or ameliorating the reduced amount of diurnal activity and/or depressive symptoms, and that the effect is caused by arachidonic acid.

Thus, in accordance with the present invention, there can be used a triglyceride containing a triglyceride (an arachidonic acid-containing triglyceride) in which part or all of the constituent fatty acid which is the active ingredient of the present invention is arachidonic acid. As an arachidonic acid-containing triglyceride, an oil (triglyceride) in which the ratio of arachidonic acid in the total fatty acids constituting the triglyceride is 20 (w/w) % or greater, preferably 30 (w/w) % or greater, more preferably 40 (w/w) % or greater, is the desired form when applied to foods. Thus, in accordance with the present invention, all of arachidonic acid-containing oils (triglycerides) that are produced by cultivating microorganisms having the ability of producing them may be used.

Microorganisms that have an ability of producing arachidonic acid-containing oils (triglycerides) include, for example, microorganisms belonging to genus *Mortierella*, genus *Conidiobolus*, genus *Pythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium* and genus *Saprolegnia*.

As microorganisms belonging to genus *Mortierella* subgenus *Mortierella*, there can be mentioned *Mortierella elongata*, *Mortierella exigua*, *Mortierella hygrophila*, *Mortierella*

*alpina*, and the like. Specifically there can be mentioned strains *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS219.35, CBS224.37, CBS250.53, CBS343.66, CBS527.72, CBS529.72, CBS608.70, and CBS754.68, and the like.

These strains are all available without limitations from the Institute of Fermentation (IFO) in Osaka City, Japan, the American Type Culture Collection (ATCC) in the U.S.A., and Centrralbureau voor Schimmelcultures (CBS). It is also possible to use *Mortierella* elongata SAM0219 (FERM P-8703) (FERM BP-1239), a microbial strain isolated from the soil by the study group of the present invention.

In order to cultivate a microbial strain for use in the present invention, spores or mycelia of the strain or a preculture obtained by pre-culturing the strain are inoculated in a liquid or solid medium and cultured. In the case of a liquid medium, the carbon sources that can be used include, but are not limited to, any of commonly used ones such as glucose, fructose, xylose, saccharose, maltose, soluble starch, molasse, glycerol, and mannitol.

As the nitrogen sources, in addition to natural nitrogen sources such as peptone, yeast extract, malt extract, meat extract, casamino acid, corn steep liquor, soybean protein, defatted soybean, and cottonseed meal, organic nitrogen sources such as urea, and inorganic nitrogen sources such as sodium nitrate, ammonium nitrate, and ammonium sulfate can be used. When desired, inorganic salts such as phosphates, magnesium sulfate, iron sulfate, and copper sulfate, and vitamins can also be used as trace nutrients. The concentrations of these medium components are not limited as long as they do not adversely affect microbial growth. Generally from the practical viewpoint, carbon sources are in the range of 0.1-40% by weight and preferably 1-25% by weight. The starting nitrogen sources added may be in the range of 0.1-10% by weight and preferably 0.1-6% by weight, and the nitrogen sources may be added through draining in the middle of culturing.

Furthermore, by controlling the concentration of the carbon source of the medium, an oil (triglyceride) containing 45 (w/w) % or more of arachidonic acid can be made the active ingredient of the present invention. Culturing days 2-4 are the microbial mass growth phase and the days after 2-4 are the oil-accumulating phase. The starting concentration of the carbon source is 1-8% by weight, preferably 1-4% by weight, and during the early period of the microbial mass growth phase and the oil-accumulating phase, the carbon source is sequentially added, with the sum of the carbon source sequentially added being 2-20% by weight, preferably 5-15% by weight. The amount added of the carbon source during the microbial mass growth phase and the early period of the oil-accumulating phase is added corresponding to the starting nitrogen source concentration and, on culturing days 7 or after, preferably culturing days 6 or after, and more preferably culturing days 4 or after, the carbon source concentration in the medium is made 0 so as to obtain an oil (triglyceride) containing 45% by weight or more of arachidonic acid, which can be made the active ingredient of the present invention.

Though the culturing temperature for arachidonic acid-producing microorganisms may vary depending on the microorganism used, after culturing at 5-40° C., preferably 20-30° C., or 20-30° C. to grow the mycelia, culturing may be continued at 5-20° C. to produce unsaturated fatty acids. By means of such a temperature control, the ratio of higher unsaturated fatty acids in the produced fatty acids can be enhanced. With pH of the medium being 4-10, preferably 5-9, aerated agitation culture, shaking culture, or stationary culture may be conducted. Culturing is usually conducted for 2-30 days, preferably 5-20 days, and more preferably 5-15 days.

Furthermore, as a means for enhancing the ratio of arachidonic acid in the arachidonic acid-containing oil (triglyceride), the arachidonic acid-containing oil may be subjected to selective hydrolysis to obtain an oil containing arachidonic acid at a high ratio, in addition to controlling the carbon source concentration in the medium. As a lipase for use in this selective hydrolysis has no site-specificity, and the hydrolytic activity decreases in proportion to the number of double bonds, ester bonds of fatty acids other than the higher unsaturated fatty acids are hydrolyzed. Also, an ester exchange reaction may occur between the resulting PUFA portion glycerides etc. thereby to yield triglycerides having an enhanced ratio of higher unsaturated fatty acids ("Enhancement of Arachidonic: Selective Hydrolysis of a Single-Cell Oil from *Mortierella* with *Candida cylindracea* Lipase": J. Am. Oil Chem. Soc., 72: 1323-1327 (1998)).

Thus, an oil (triglyceride) containing arachidonic acid at a high ratio obtained by selective hydrolysis of an arachidonic acid-containing oil may be made the active ingredient of the present invention. The ratio of arachidonic acid relative to the total fatty acids of the arachidonic acid-containing oil (triglyceride) of the present invention is preferred to be high for the purpose of eliminating the effect of other fatty acids. However, the present invention is not limited to high ratios, but in practice, the absolute amount of arachidonic acid may sometimes count when application into foodstuffs is to be contemplated, and even an oil (triglyceride) containing 10% by weight or more of arachidonic acid can, substantially, be used.

Furthermore, as a triglyceride in which part or all of the constituent fatty acids is arachidonic acid, there can be used a triglyceride wherein a middle-chain fatty acid is bound at positions 1 and 3 and arachidonic acid is bound at position 2. There can also be used an oil (triglyceride) that contains 5 mole % or more, preferably 10 mole % or more, more preferably 20 mole % or more, and most preferably 30 mole % of a triglyceride wherein a middle-chain fatty acid is bound at positions 1 and 3 and arachidonic acid is bound at position 2. The above middle-chain fatty acid that is bound at positions 1 and 3 can be selected from fatty acids having 6-12 carbons. As fatty acids having 6-12 carbons, there can be mentioned caprilic acid and caproic acid etc., and 1,3-capriloyl-2-arachidonoyl-glycerol (referred to hereinafter as "8A8") is specifically preferred.

When elderly people are the subject, these triglycerides wherein a middle-chain fatty acid is bound at positions 1 and 3 and arachidonic acid is bound at position 2 are best oils (triglycerides). Generally when oils (triglycerides) are ingested and transported into the small intestine, they are hydrolyzed with pancreatic lipase, in which said pancreatic lipase is site-specific for positions 1 and 3, and the positions 1 and 3 of the triglyceride are cleaved to form 2 molecules of free fatty acids and one molecule of 2-monoacylglycerol (2-MG) at the same time. As this 2-MG has a very high activity of dissolving bile acid and is highly absorptive, the position 2 fatty acid is said to be more absorptive. When 2-MG is dissolved in bile acid, it also serves as a surfactant and enhances the absorptive property of free fatty acids.

Then, free fatty acids and 2-MG in combination with cholesterol and phospholipids etc. biosynthesize bile acid composite micelle, which is incorporated into intestinal epithelial cells where triacyl glycerol is formed again and finally released as chylomicron into the lympha. The characteristics of pancreatic lipase for fatty acids is higher for saturated fatty acids, and arachidonic acid is hardly cleavable. A further problem is that the pancreatic lipase activity decreases with aging, and thus for the elderly people, triglycerides wherein a middle-chain fatty acid is bound at positions 1 and 3 and arachidonic acid is bound at position 2 become the best oils (triglycerides).

As a specific method of producing a triglyceride wherein a middle-chain fatty acid is bound at positions 1 and 3 and arachidonic acid is bound at position 2, a lipase that only acts on an ester bond at positions 1 and 3 of a triglyceride is acted in the presence of an arachidonic acid-containing oil (triglyceride) and a middle-chain fatty acid.

A raw material oil (triglyceride) is a triglyceride having arachidonic acid as a constituent fatty acid. When the ratio of arachidonic acid relative to the total fatty acids constituting the triglyceride is high, the reaction temperature is preferably higher than the usual enzyme reaction temperature of 20-30° C., that is 30-50° C., preferably 40-50° C., in order to prevent a reduction of the reaction yield due to the increased ratio of unreacted oils (the raw material triglyceride and triglycerides in which only one of the fatty acids at positions 1 and 3 is a middle-chain fatty acid).

As lipases that specifically act on the ester bond at positions 1 and 3 of triglycerides, there can be mentioned those produced by microorganisms belonging to genus *Rhizopus*, genus *Rhizomucor*, genus *Aspergillus* etc., and porcine pancreatic lipase, and the like. Such lipases are commercially available. For example, a lipase (Talipase manufactured by Tanabe Seiyaku Co., Ltd.) from *Rhizopus delemar*, a lipase (Rhibozyme IM manufactured by NovoNordisk Pharma Co., Ltd.) from *Rhizomucor miehei*, a lipase (Lipase A, manufactured by Amano Enzyme Inc.) from *Aspergillus niger* and the like can be mentioned, but they are not limiting, and any lipases that are site-specific for positions 1 and 3 can be used.

Since the above lipases are used at a reaction temperature of 30° C. or more, preferably 40° C. or more in order to enhance reaction efficiency, it is preferred to use a lipase that is immobilized on an immobilization carrier in order to impart heat resistance to the enzymes. As an immobilization carrier, there can be mentioned an ion exchange resin that is a high porous resin and has a pore size of about 100 angstroms or more, such as Dowex MARATHON WBA. It is not limiting, however, and any immobilization carrier that can impart heat resistance may be used.

0.5-20 parts by weight of a lipase specific for positions 1 and 3 is suspended in one part of an immobilization carrier, and 2-5 parts by volume of cold acetone (for example −80° C.) is added gradually under stirring to form a precipitate. The precipitate can be dried under reduced pressure to prepare an immobilized enzyme. In a simpler method, 0.05-0.4 parts by weight of a lipase specific for positions 1 and 3 is dissolved in a minimum amount of water, and an immobilized carrier is mixed under stirring, and dried under reduced pressure to prepare an immobilized enzyme. By this procedure about 90% of lipase is immobilized to a carrier, but this per se does not exhibit any ester exchange activity, and preferably it is pretreated in a substrate to which water has been added at 1-10 weight (w/v) %, preferably 1-3 weight (w/v) %, so that the immobilized enzyme can be best activated and subjected to manufacture.

Depending on the type of enzyme, the amount of water added to the aqueous reaction system is very important. When there is no water, ester exchange does not easily occur, and when there is plenty of water, hydrolysis occurs so that the recovery of glycerides becomes reduced (when hydrolysis occurs, diglycerides and monoglycerides are formed). In this case, however, by using the immobilized enzyme activated in the pretreatment, the amount of water added to the present reaction system becomes unimportant, and the ester exchange reaction can occur in high efficiency even in a water-free system. Furthermore, by selecting the type of enzymes, pretreatment can be omitted.

Thus, by using a heat-resistant immobilized enzyme and thus enhancing the temperature of the enzyme reaction, a triglyceride (8A8) in which a middle-chain fatty acid is bound at positions 1 and 3 and arachidonic acid is bound at position 2 can be efficiently produced without lowering the reaction efficiency even for arachidonic acid-containing oils (triglycerides) that has a low reactivity for lipases specific for positions 1 and 3.

In methods of producing foods and drinks that have an activity of ameliorating the reduced amount of diurnal activity and/or depressive symptoms, arachidonic acid and/or a compound having arachidonic acid as a constituent fatty acid can be used alone or blended with a raw material for foods and drinks that contains little or a very small amount, if any, of arachidonic acid. The very small amount as used herein means the amount that, even when the raw material for foods and drinks contains arachidonic acid and a food composition having the material blended therein is ingested by humans, it does not reach the daily intake (described hereinafter) of arachidonic acid per day of the present invention.

In the case of a triglyceride in which part or all of the constituent fatty acids is arachidonic acid, oils (triglycerides) have numerous potentials in this application, and can be used as raw materials and additives for foods, beverages, cosmetics, and pharmaceuticals. The intended use and the amount used has no limitation.

For example, as food compositions there can be mentioned functional foods, nutrient supplements, foods for specified health uses, modified milk for premature infants, modified milk for babies, baby foods, foods for pregnant women or foods for the elderly people and the like, in addition to general foods. As examples of foods containing oils, there can be mentioned natural foods that originally contain oils such as meat, fish and nuts, foods to which oils are added at the time of cooking such as soup, foods for which oils are used as a heat medium such as donuts, fatty foods such as butter, processed foods to which oils are added at the time of processing such as cookies, or foods to which oils are sprayed or applied at the finish of processing such as hard biscuits, and the like. Furthermore, oils may be added to agricultural foods, fermented foods, livestock food products, aquatic foods, or beverages that contain no oils. Furthermore, they may be in the form of functional foods or pharmaceuticals, and may also be a processed form such as enteral foods, powders, granules, troches, oral liquids, suspensions, emulsions, syrups and the like. The product of the present invention may have attached a label indicating that it has an activity of ameliorating the reduced amount of diurnal activity and/or depressive symptoms.

The composition of the present invention may contain various carriers and additives that are generally used for foods or drinks, pharmaceuticals or quasi drugs in addition to the active ingredient of the present invention. Specifically it is preferred to contain antioxidants in order to prevent oxidation of the active ingredient of the present invention. As antioxidants, there can be mentioned naturally occurring antioxidants such as tocopherols, flavone derivatives, phyllodulcins, kojic acid, gallic acid derivatives, catechins, fuki acid, gossypol, pyrazine derivatives, sasamol, guaiacol, guaiac acid, p-coumaric acid, nordihydroguaiatic acid, sterols, terpenes, nucleobases, carotenoids and lignins, and synthetic antioxidants represented by ascorbate-palmitate ester, ascorbate-stearate ester, butyl hydroxy anisole (BHA), butyl hydroxy toluene (BHT), t-butylhydroquinone (TBHQ), and 4-hydroxymethyl-2,6-di-t-butylphenol (HMBP).

As tocopherols, α-tocopherol, β-tocopherol, γ-tocopherol, δ-tocopherol, ε-tocopherol, ζ-tocopherol, η-tocopherol, and tocopherol esters (tocopherol acetates etc.) may be mentioned as related compounds. As carotenoids, there can be mentioned, for example, β-carotene, canthaxantin, astaxanthin and the like.

As carriers, the composition of the present invention can include, in addition to the active ingredient of the present invention, various carriers, extender agents, diluents, bulking agents, dispersants, excipients, binding solvents (for example water, ethanol, vegetable oils), dissolution adjuvants, buffers, dissolution-promoting agents, gelling agents, suspending agents, wheat flour, rice flour, starch, corn starch, polysaccharides, milk proteins, collagen, rice oils, lecithin and the like. As additives, it can include, but not limited to, vitamins, sweeteners, organic acids, coloring agents, perfumes, anti-wetting agents, fibers, electrolytes, minerals, nutrients, antioxidants, preservatives, flavoring agents, wetting agents, extracts of natural foods, vegetable extracts and the like.

The main pharmaceutically active ingredient of arachidonic acid and a compound which has an arachidonic acid as a constituent fatty acid is arachidonic acid. It is reported that the daily dietary intake of arachidonic acid is 0.14 g in the Kanto area and 0.19-0.20 g in the Kansai area [Sisitsu Eiyougaku (Lipid Nutrition) 4: 73, (1995)]. In the case of the elderly people who tend to take reduced amounts of oils and their pancreatic lipase activity tends to be reduced, a significant amount or more of arachidonic acid must be ingested. Thus, the daily intake of arachidonic acid and a compound having arachidonic acid as a constituent fatty acid by a human adult (having, for example, a body weight of 60 kg) is, in terms of arachidonic acid, 0.001 g-20 g, preferably 0.01 g-10 g, more preferably 0.05 g-5 g, and most preferably 0.1 g-2 g.

When the active ingredient of the present invention is actually applied into foods or drinks, the absolute amount of arachidonic acid that is blended with the foods or drinks is important. However, when a triglyceride containing a triglyceride in which part or all of the constituent fatty acids is arachidonic acid is blended to a food, it is blended to 0.001% by weight or more, preferably 0.01% by weight or more, and more preferably 0.1% by weight or more as arachidonic acid, because the absolute amount to be blended to a food or drink may vary with the amount ingested, of the blended food or a drink. Furthermore, when a triglyceride in which a middle-chain fatty acid is bound at positions 1 and 3 and arachidonic acid is bound at position 2 is blended to a food, it is blended to 0.0003% by weight or more, preferably 0.003% by weight or more, more preferably 0.03% by weight or more.

When the composition of the present invention is used as a pharmaceutical product, it can be produced according to a method commonly used in the field of pharmacy, for example a method described in the Japanese Pharmacopoeia or a method in conformity therewith.

When the composition of the present invention is used as a pharmaceutical product, the amount blended, of the active ingredient in the composition, is not specifically limited and can be used at a suitable blend ratio, as appropriate, as long as the purpose of the present invention is attained.

When the composition of the present invention is used as a pharmaceutical product, preferably it is administered in a unit dosage form and, specifically, it is orally administered. Dosage of the composition of the present invention may differ with age, body weight, disease condition, administration frequency etc., and the daily dosage of arachidonic acid and/or a compound having arachidonic acid as a constituent fatty acid of the present invention for an adult (about 60 kg), in terms of arachidonic acid, is generally about 0.001 g-20 g, preferably 0.01 g-10 g, more preferably 0.05 g-5 g, and most preferably 0.1 g-2 g which may be daily administered in 1-3 divided doses.

The major fatty acids of phospholipids in the cell membrane of the brain are arachidonic acid and docosahexaenoic acid and, considering the balance, docosahexaenoic acid is preferably combined. Also, as the ratio of eicosapentaenoic acid in the phospholipid membrane of the brain is very low, the combination of arachidonic acid and docosahexaenoic acid with little eicosapentaenoic acid is preferred. In the combination of arachidonic acid and docosahexaenoic acid, the ratio of arachidonic acid/docosahexaenoic acid is in the range of 0.1-15, and preferably in the range of 0.25-10. Furthermore, foods and drinks in which eicosapentaenoic acid has been blended at an amount not exceeding one fifth (weight ratio) of arachidonic acid is preferred.

EXAMPLES

The present invention will now be explained in more details with reference to specific examples. It should be noted, however, that the present invention is not limited by these examples in any way.

Example 1

A method of Producing an Arachidonic Acid-Containing Triglyceride

As the arachidonic acid-producing microorganism, *Mortierella alpina* CBS754.68 was used. Six kiloliters of a medium containing 1.8% glucose, 3.1% defatted soy bean flour, 0.1% soy bean oil, 0.3% $KH_2PO_4$, 0.1% $Na_2SO_4$, 0.05% $CaCl_2/2H_2O$, and 0.05% $MgCl_2/5H_2O$ was prepared in a 10 kL culture tank, and the starting pH was adjusted to 6.0. 30 L of a preculture was inoculated, and was subjected to an aerated stirring culture at a condition of 26° C., an aeration rate of 360 m$^3$/h, a tank pressure of 200 kPa for 8 days. The agitation rate was adjusted so as to maintain the concentration of dissolved oxygen at 10-15 ppm. Furthermore, the glucose concentration was maintained to be within 1-2.5% by the draining method until day 4, and within 0.5-1% thereafter (the above % means weight (W/V) %).

After the completion of culturing, filtration and drying was conducted to obtain a mycelia containing triglycerides having arachidonic acid as a constituent fatty acid and, by hexane extraction of the mycelia, oil was extracted and, via a purification process (degumming, deacidification, deodorization, depigmentation), 150 Kg of an arachidonic acid-containing triglyceride (triglyceride in which part or all of the constituent fatty acid is arachidonic acid) was obtained. The oil (triglyceride) obtained was methylesterified, and the fatty acid methyl ester obtained was analyzed by gas chromatography, which indicated that the ratio of arachidonic acid in the total fatty acids was 40.84% by weight.

The ratio of palmitic acid, stearic acid, oleic acid, linoleic acid, γ-linolenic acid, dihomo-γ-linolenic acid was 11.63%, 7.45%, 7.73%, 9.14%, 2.23%, and 3.27%, respectively. Furthermore, the above arachidonic acid-containing oil (triglyceride) (SUNTGA40S) was ethylesterified, and the fatty acid ethyl ester mixture containing 40% by weight of the arachidonic acid ethyl ester was subjected to standard high performance liquid chromatography to separate and purify 99% by weight of arachidonic acid ethyl ester.

Example 2

Production of a Triglyceride Containing 5 Mole % or More of 8A8

100 g of an ion exchange resin (Dowex MARATHON WBA: Dow Chemical) was suspended in 80 ml of an aqueous solution of *Rhizopus delemar* lipase (12.5% Talipase powder manufactured by Tanabe Seiyaku Co., Ltd.) and was stirred in 240 ml of a cold acetone (for example, at −80° C.), followed by drying under reduced pressure to obtain an immobilized lipase.

Then, 80 g of triglyceride (SUNTGA40S) containing 40% by weight of arachidonic acid obtained in Example 1, 160 g of caprilic acid, 12 g of the above immobilized lipase, and 4.8 ml of water were reacted under stirring (130 rpm) at 30° C. for 48 hours. After the reaction was complete, the reaction liquid was removed to obtain an activated immobilized enzyme.

Then, 10 g of the immobilized lipase (*Rhizopus delemar* lipase, carrier: Dowex MARATHON WBA) was charged into a jacketed glass column (1.8×12.5 cm, volume 31.8 ml), to which a reaction oil obtained in Example 1 in which SUNTGA40S and caprilic acid were mixed at 1:2 was passed at a constant rate (4 ml/h) and subjected to a continuous reaction to obtain 400 g of a reacted oil. The column temperature was 40-41° C. From the reacted oil obtained, unreacted caprilic acid and free fatty acids were removed by molecular distillation and, via a purification process (degumming, deacidification, deodorization, depigmentation) for edible oils, an oil (triglyceride) containing 8A8 was obtained.

Using gas chromatography and a high performance liquid chromatography, the ratio of 8A8 in the 8A8-containing oil (triglyceride) obtained was investigated and was found to be 31.6 mole % (the ratio of 8P8, 8O8, 8L8, 8G8 and 8D8 was 0.6, 7.9, 15.1, 5.2 and 4.8 mole %, respectively. The fatty acid P, O, L, G and D in which triglyceride is bound at position 2 refers to palmitic acid, oleic acid, linoleic acid, γ-linolenic acid and dihomo-γ-linolenic acid, respectively, and 8P8 refers to 1,3-capriloyl-2-palmitolein-glycerol, 8O8 refers to 1,3-capriloyl-2-oleoyl-glycerol, 8L8 refers to 1,3-capriloyl-2-linoleoil-glycerol, 8G8 refers to 1,3-capriloyl-2-γ-linolenoyl-glycerol, and 8D8 refers to 1,3-capriloyl-2-dihomo-γ-linolenoyl-glycerol). From the 8A8-containing oil (triglyceride) obtained, 96 mole % 8A8 was separated and purified by a standard high performance liquid chromatography.

Example 3

Production of a Test Capsule

Water was added to 100 parts by weight of gelatin and 35 parts by weight of food additive glycerin and dissolved at 50-60° C. to prepare a gelatin coat with a viscosity of 2000 cp. Then vitamin E oil was mixed to 0.05% by weight in the arachidonic acid-containing oil (triglyceride) obtained in Example 1 to prepare content 1. The content 1 was used to form capsules, which were then dried to prepare soft capsules containing 200 mg of the content per capsule. As placebo capsules for tests on humans, soft capsules in which the content was replaced with olive oil were prepared at the same time.

Example 4

Ingestion Study on the Effect of an Arachidonic Acid-Containing Edible Oil Capsule on the Reduced Amount of Diurnal Activity and/or Depressive Symptoms of Elderly People Staying at an Aged-Care Facility for a Short Period The amount of diurnal and nocturnal activity was measured by wearing a wristwatch-type measuring device that has built in a sensor for measuring the amount of activity on the nondominant arm to measure the amount of night and day activity continuously for one week. By analyzing the result of this actigraph measurement by a computer software, the amount of activity and the quality of night sleep etc. were evaluated. The study on humans of the present invention was conducted under careful consideration in pursuant to the Helsinki Declaration.

After a briefing on the consent of entry into the study, seven elderly individuals who consented and who were staying at an aged care facility for a short period were divided into two groups: A: N=4, B: N=3. In order to ingest 240 mg of arachidonic acid per day, Group A received three capsules containing an arachidonic acid-containing edible oil (80 mg/capsule in terms of arachidonic acid) prepared in Example 3 daily for one month, and Group B received three placebo capsules. Before and after capsule intake, the actigraph was worn on the nondominant arm to measure the amount of night and day activity continuously for one week. Then the subjects in Group A and Group B stopped taking in the capsules for 2 weeks as a washout period. After the wash out, Group A received the placebo capsules and Group B received capsules containing an arachidonic acid-containing edible oil for one month. Similarly, before and after capsule intake, the actigraph was worn on the nondominant arm to measure the amount of night and day activity continuously for one week (a double blind test, a crossover test).

At the same time, before and after capsule intake, a test using the scoring of the Zung self-rating depression scale was performed to assess the degree of depression. Using the test by the Zung self-rating depression scale (40 or more: mild depression, 50 or more: medium depression), the degree of depression was assessed.

Changes in the mean amount of diurnal activity before and after capsule intake are shown in FIG. 1, and changes in scores by the Zung self-rating depression scale are shown in FIG. 2. When placebo capsules were taken, no significant changes were noted in both the mean amount of diurnal activity and scores by the Zung self-rating depression scale. But when capsules containing an arachidonic acid-containing edible oil were taken, it was revealed, the mean amount of diurnal activity significantly increased to 19.1 counts/day and the score by the Zung self-rating depression scale significantly improved by 3.2.

Then, the correlation of the mean amount of diurnal activity and scores by the Zung self-rating depression scale was determined by a linear approximate curve based on the least square method (FIG. 3). A significant correlation (coefficient of correlation R=−0.561) was noted between the mean amount of diurnal activity and scores by the Zung self-rating depression scale, which revealed that the amelioration of the degree of depression leads to increased diurnal activity though the mean score by the original Zung self-rating depression scale is 37.6 which is a degree not reaching mild depression. Thus, it has been demonstrated for the first time that the intake of an arachidonic acid-containing edible oil can ameliorate the reduced amount of diurnal activity and/or depressive symptoms, and that the effect is caused by arachidonic acid.

Example 5

Preparative Example of Arachidonic Acid-Containing Edible Oil (Triglyceride)-Blended Capsules Water was added to 100 parts by weight of gelatin and 35 parts by weight of food additive glycerin and dissolved at 50-60° C. to prepare a gelatin coat with a viscosity of 2000 cp. Then vitamin E oil was mixed to 0.05% by weight in the oil (triglyceride) containing 32 mole % of 8A8 obtained in Example 2 to prepare content 2. 50% by weight of the arachidonic acid-containing oil (triglyceride) obtained in Example 1 and 50% by weight of a fish oil (tuna oil: the ratio of eicosapentaenoic acid and docosahexaenoic acid in the total fatty acids is 5.1% and 26.5%, respectively) were mixed, and then vitamin E oil was mixed thereto to 0.05% by weight to prepare content 3.

80% by weight of the arachidonic acid-containing oil (triglyceride) and 20% by weight of the fish oil (tuna oil: the ratio of eicosapentaenoic acid and docosahexaenoic acid in the total fatty acids is 5.1% and 26.5%, respectively) were mixed, and then vitamin E oil was mixed thereto to 0.05% by weight to prepare content 4. To a 99% arachidonic acid ethyl ester prepared in Example 1, vitamin E oil was mixed to 0.05% by weight to prepare content 5. Using these contents 2-5, capsules were formed and dried according to standard methods to prepare soft capsules containing 180 mg of the content per capsule.

Example 6

Use in an Oil Infusion 400 g of the oil (triglyceride) containing 96 mole % of 8A8 obtained in Example 2, 48 g of purified egg yolk lecithin, 20 g of oleic acid, 100 g of glycerin and 40 ml of 0.1N sodium hydroxide were added and dispersed by a homogenizer, and then distilled water for injection was added to make 4 liters. This was emulsified using a high-pressure spray-type emulsifying machine to prepare an oil emulsion. After said oil emulsion was dispensed in 200 ml aliquots into plastic bags, they were subjected to high-pressure steam sterilization at 121° C. for 20 minutes to prepare an oil infusion.

Example 7

Use in a Juice

Two grams of β-cyclodextrin were added to 20 ml of an aqueous solution of 20% ethanol, to which 100 mg of the arachidonic acid-containing triglyceride (vitamin E being blended to 0.05%) obtained in Example 1 was added under stirring with a stirrer, and incubated at 50° C. for 2 hours. After cooling to room temperature (for about 1 hour), it was further incubated while stirring at 4° C. for 10 hours. The precipitate formed was recovered by centrifugation, washed in n-hexane, and lyophilized to obtain 1.8 g of a cyclodextrin inclusion compound containing an arachidonic acid-containing triglyceride. One gram of this powder was homogenously mixed with 10 L of a juice to prepare a juice containing an arachidonic acid-containing triglyceride.

The invention claimed is:

1. A method of treating depression resulting from sleep disorders that are caused by a mental disease or a neurological disease, comprising administering an effective amount of a composition to a human subject having the depression, wherein the composition comprises arachidonic acid and/or a compound having arachidonic acid as a constituent fatty acid, wherein the effective amount of the composition includes 240 mg of arachidonic acid per day.

2. The method of claim 1, wherein the compound having arachidonic acid as a constituent fatty acid is an alcohol ester of arachidonic acid or a triglyceride, a phospholipid, or a glycolipid in which part or all of the constituent fatty acid is arachidonic acid.

3. The method of claim 2, wherein the triglyceride in which part or all of the constituent fatty acid is arachidonic acid is a triglyceride in which a middle-chain fatty acid is bound at positions 1 and 3 and arachidonic acid is bound at position 2, wherein the middle-chain fatty acid is one selected from fatty acids having 6-12 carbons.

4. The method of claim 1, wherein the composition comprises triglycerides that contain a triglyceride in which part or all of the constituent fatty acid is arachidonic acid.

5. The method of claim 4, wherein the ratio of arachidonic acid in the triglycerides that contain a triglyceride in which part or all of the constituent fatty acid is arachidonic acid is 10% by weight or more relative to the total fatty acids constituting the triglycerides.

6. The method of claim 4, wherein the triglycerides that contain a triglyceride in which part or all of the constituent fatty acid is arachidonic acid are extracted from a microorganism belonging to genus *Mortierella*, genus *Conidiobolus*, genus *Pythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium* and genus *Saprolegnia*.

7. The method of claim 4, wherein the triglycerides that contain a triglyceride in which part or all of the constituent fatty acid is arachidonic acid are triglycerides containing eicosapentaenoic acid at an amount not exceeding one fifth (weight ratio) of arachidonic acid.

8. The method of claim 1, wherein the composition comprises triglycerides that contain 5 mole % or more of a triglyceride in which a middle-chain fatty acid is bound at positions 1 and 3 and arachidonic acid is bound at position 2, wherein the middle-chain fatty acid is one selected from fatty acids having 6-12 carbons.

9. The method of claim 1, wherein the mental disease is schizophrenia or depression.

10. The method of claim 1, wherein the neurological disease is cerebral degenerative diseases, dementia, or Parkinson's disease.

11. The method of claim 1, wherein the composition is a food composition or a pharmaceutical composition.

12. The method of claim 11, wherein the food composition is a functional food, nutrient supplement, modified milk for premature infants, modified milk for babies, baby food, food for pregnant women, or food for elderly people.

13. The method of claim 1, wherein the composition further comprises docosahexaenoic acid or a compound having docosahexaenoic acid as a constituent fatty acid.

14. The method of claim 13, wherein the compound having docosahexaenoic acid as a constituent fatty acid is an alcohol ester of docosahexaenoic acid or a triglyceride, a phospholipid or a glycolipid in which part or all of the constituent fatty acid is docosahexaenoic acid.

15. The method of claim 13, wherein the weight ratio of arachidonic acid/docosahexaenoic acid in the combination of said arachidonic acid and said docosahexaenoic acid is in the range of 0.1-15.

* * * * *